(12) United States Patent
Orbay et al.

(10) Patent No.: US 11,344,341 B2
(45) Date of Patent: May 31, 2022

(54) INTRAMEDULLARY FIXATION NAIL AND METHOD OF USE

(71) Applicant: Skeletal Dynamics, Inc., Miami, FL (US)

(72) Inventors: Jorge L. Orbay, Miami, FL (US); Raul Galindo, Miami, FL (US)

(73) Assignee: SKELETAL DYNAMICS, INC., Miami, FL (US)

( * ) Notice: Subject to any disclaimer, the term of this patent is extended or adjusted under 35 U.S.C. 154(b) by 0 days.

(21) Appl. No.: 17/076,661

(22) Filed: Oct. 21, 2020

(65) Prior Publication Data

US 2021/0121209 A1  Apr. 29, 2021

Related U.S. Application Data

(60) Provisional application No. 62/926,156, filed on Oct. 25, 2019.

(51) Int. Cl.
| | | |
|---|---|---|
| *A61B 17/72* | (2006.01) | |
| *A61B 17/17* | (2006.01) | |
| *A61B 17/92* | (2006.01) | |

(52) U.S. Cl.
CPC .......... *A61B 17/72* (2013.01); *A61B 17/1717* (2013.01); *A61B 17/1725* (2013.01); *A61B 17/7291* (2013.01); *A61B 17/921* (2013.01)

(58) Field of Classification Search
CPC .......................................... A61B 17/72–7291
See application file for complete search history.

(56) References Cited

U.S. PATENT DOCUMENTS

| | | | | |
|---|---|---|---|---|
| 4,091,806 A | * | 5/1978 | Aginsky | A61B 17/7225 606/63 |
| 4,875,474 A | | 10/1989 | Border | |
| 5,573,536 A | * | 11/1996 | Grosse | A61B 17/72 606/60 |
| 2002/0156473 A1 | * | 10/2002 | Bramlet | A61B 17/744 606/62 |
| 2007/0156144 A1 | | 7/2007 | Ulrich et al. | |

(Continued)

OTHER PUBLICATIONS

International Application No. PCT/US20/56799—Patent Cooperation Treaty PCT International Search Report—Completed Dec. 31, 2020 (dated Feb. 5, 2021).

(Continued)

*Primary Examiner* — Nicholas J Plionis
(74) *Attorney, Agent, or Firm* — Lott & Fischer, PL

(57) ABSTRACT

Disclosed is an intramedullary nail comprising a shaft having a length, a constant diameter, an exterior bone contacting surface, a leading (or distal) end and a trailing (or proximal) end, wherein the leading end is progressively tapered and comprises a well or cup, adapted to receive the tip of a standard K-wire, the trailing end comprises a driving fitting adapted for attachment to a driving tool for insertion of the nail into the prepared bone, the trailing end may optionally include an internal thread that can be used to secure the nail to a drill guide which can also function as an insertion handle, and the nail's shaft may also optionally be equipped with threaded and/or unthreaded cross-drilled holes for insertion of unicortical locking screws and bone screws, respectively, once the nail is placed as desired.

8 Claims, 13 Drawing Sheets

(56) References Cited

U.S. PATENT DOCUMENTS

| | | | |
|---|---|---|---|
| 2014/0088595 A1* | 3/2014 | Mueckter | A61B 17/744 606/64 |
| 2016/0206355 A1 | 7/2016 | Robledo | |
| 2019/0175232 A1* | 6/2019 | Karg | A61B 17/744 |

OTHER PUBLICATIONS

International Application No. PCT/US20/39183—Patent Cooperation Treaty PCT Written Opinion of the International Searching Authority—Completed Dec. 31, 2020 (dated Feb. 5, 2021).

* cited by examiner

INTRAMEDULLARY FIXATION NAIL AND METHOD OF USE

CLAIM OF PRIORITY

This application is being filed as a non-provisional patent application under 35 U.S.C. § 111(a) and 37 CFR § 1.53(b). This application claims priority under 35 U.S.C. § 119(e) to U.S. provisional patent application Ser. No. 62/926,156 filed on Oct. 25, 2019, the contents of which are incorporated herein by reference.

FIELD OF INVENTION

The invention relates generally to bone fusion devices and systems, and, in particular, to an intramedullary bone fixation nail adapted to interface with Kirschner wires or pins ("K-wires") for easier, more accurate, and more efficient placement of the bone fixation nail at the desired location.

BACKGROUND OF THE INVENTION

Intramedullary fixation nails are known in the art. It is known to implant unthreaded rods or nails within the medullar region of a fractured bone, or of reduced fragments of a broken bone, in order to stabilize the bone while it heals. The common procedure for implanting such a device is to form an opening on one end of the fractured or broken bone, the opening extending into the medulla and through the fracture or break. This initial opening is commonly formed by using a K-wire which is a smooth steel pin that is inserted into the bone as a guide for insertion of the nail. The fracture or break is then reduced. A cannulated drill, using the K-wire as a guide, is then used to expand the opening made using the K-wire to a width suitable for insertion of the nail. The K-wire is then pushed out simultaneously as the nail is then inserted into the bone.

One shortcoming of known intramedullary nails is that problems often arise during insertion of the nail because once the K-wire is removed, and before the nail is inserted, debris, tissue and fluid may become trapped inside the opening formed in the bone. In fact, debris, tissue, and fluid may completely obscure or cover up the opening and make it difficult, if not impossible, to insert the nail without further clearing.

Further, any debris, tissue or fluid that is trapped inside the bone may interfere with the functioning of the nail, inhibit bone growth, create a risk for infection, and prevent the precise determination of whether the nail has been placed in the correct position.

SUMMARY OF THE INVENTION

It is an object of the instant invention to provide an intramedullary bone fixation nail that is adapted to cooperate with a K-wire to easily and efficiently insert the nail into a fractured or broken bone while significantly reducing the possibility of debris, tissue, and/or fluid being trapped in the opening made in the bone to accommodate the nail. In operation, the nail disclosed herein pushes out the K-wire from the medullary canal while the nail is simultaneously inserted.

The disclosed intramedullary nail comprises a shaft having a length, a constant diameter, and an exterior bone contacting surface. The nail further comprises a leading (or distal) end and a trailing (or proximal) end. The leading end is progressively tapered for ease of insertion, being atraumatic in design and comprises a well or cup, adapted to receive the tip of a standard K-wire. The well or cup of the leading end may optionally include internal threads adapted to mate with a removal tool. The trailing end comprises a driving fitting adapted for attachment to a driving tool for insertion of the nail into the prepared bone. The trailing end may optionally include an internal thread that can be used to secure the nail to a drill guide which can also function as an insertion handle. The nail's shaft may also optionally be equipped with threaded and/or unthreaded cross-drilled holes for insertion of locking compression screws and transfixion screws, respectively, once the nail is placed as desired.

DETAILED DESCRIPTION OF THE INVENTION

Figure 1A:
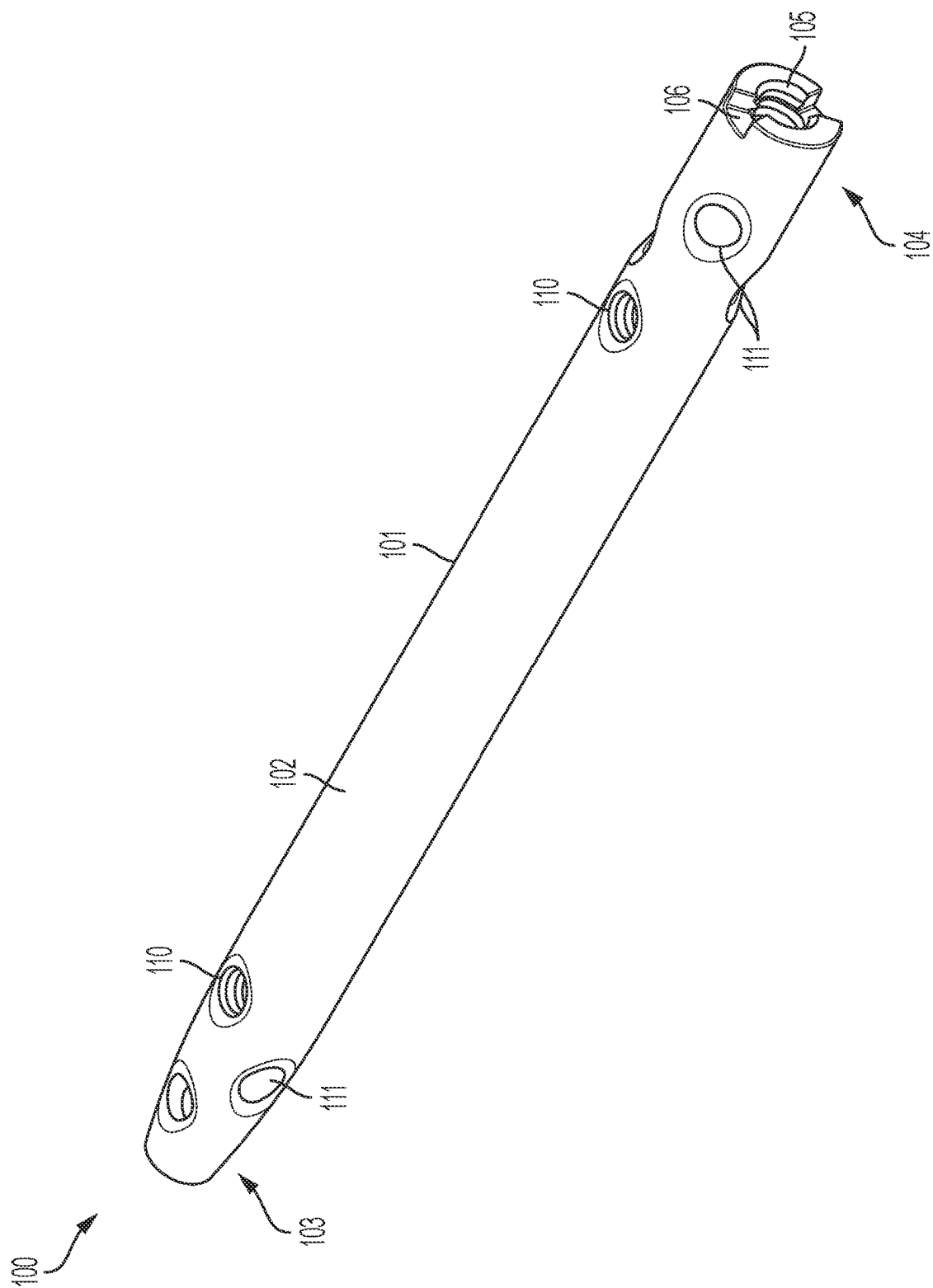
FIGS. 1A-1B are rear isometric, and front isometric views, respectively, of an embodiment of the intramedullary nail of the present invention.
Figure 1B:
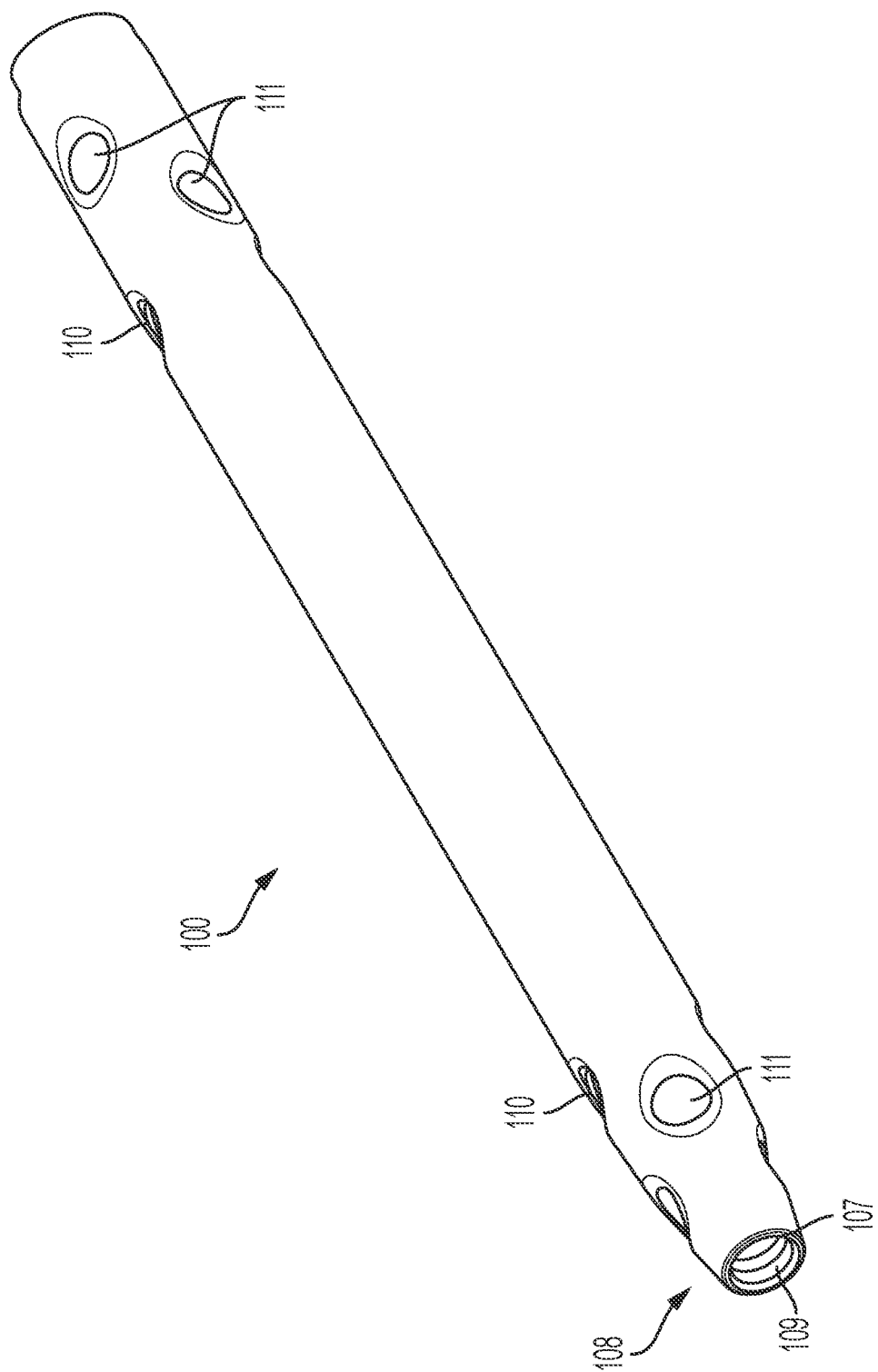

Referring now to FIGS. 1A-1B, therein are shown several views of an intramedullary nail (100) according to one embodiment of the present invention. The intramedullary nail (100) comprises an elongated shaft (101) having an exterior bone contacting surface (102), a leading (or distal) end (103), a trailing (or proximal) end (104).

Figure 3A:
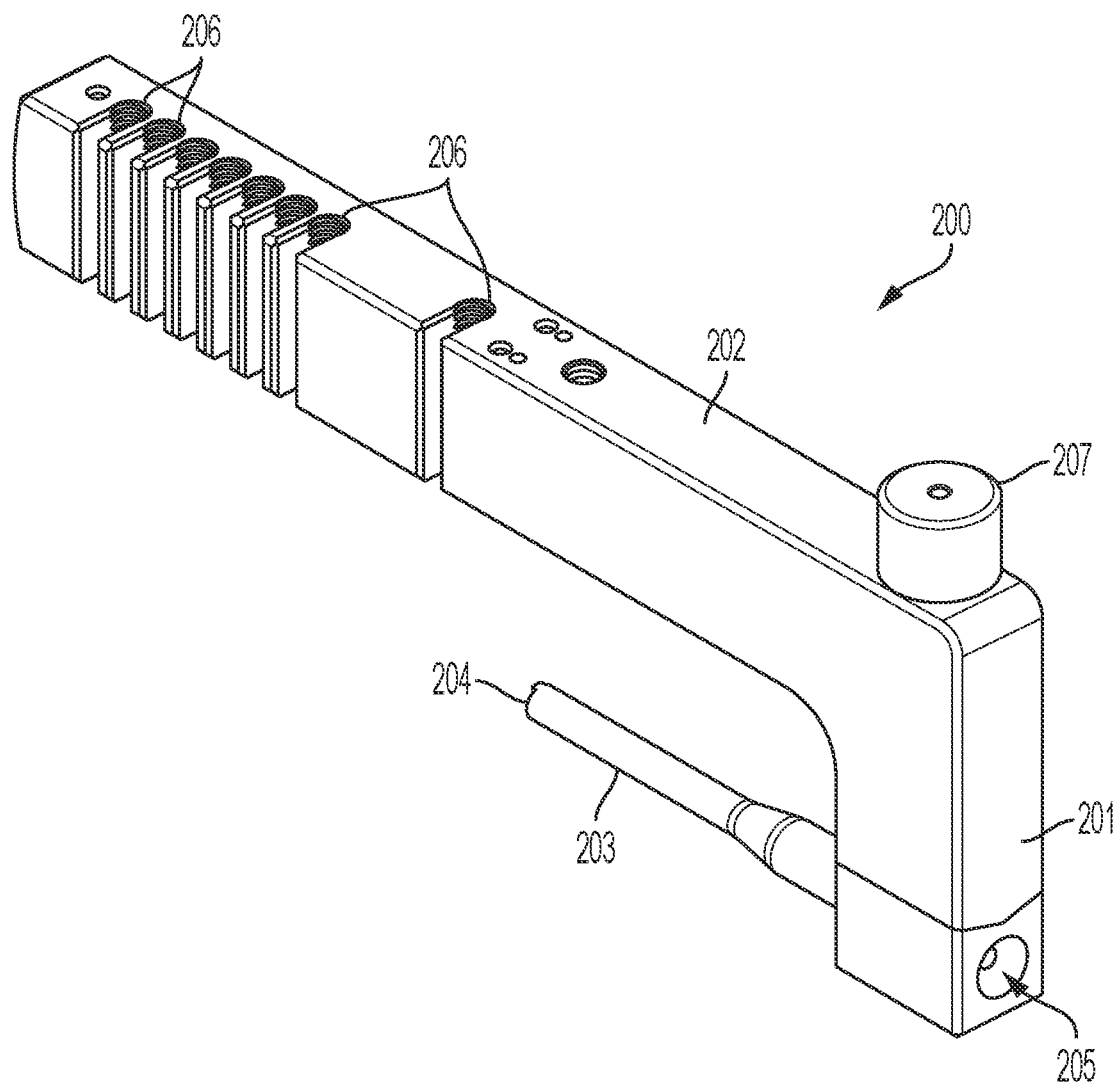
FIGS. 3A-3B are rear isometric views of an embodiment of the combination drill guide/insertion handle intramedullary nail of the present invention and a detailed view of nail implant attachment to drill guide/insertion handle.
Figure 3B:
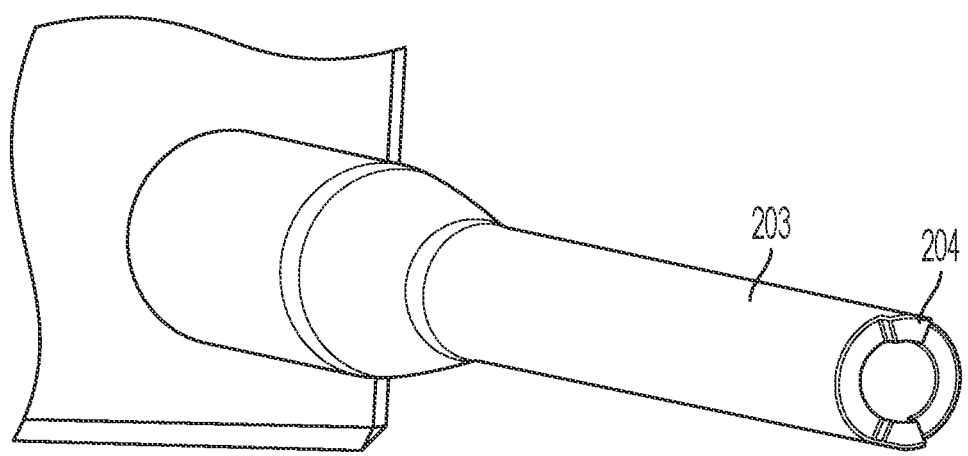

The trailing end (104) comprises an internal thread (105) and an anti-rotational feature (106) adapted to mate with a corresponding feature (204) on the combination drill guide/insertion handle (200) (See FIG. 3A-3B). The internal thread is adapted to mate with the corresponding threaded tip (303) of the locking screw (300) (See FIG. 4).

The leading end (103) comprises a well or cup (107) which is adapted to accept a K-Wire tip upon insertion into the bone. The leading end may also include internal thread (109) adapted to mate with a removal tool (not shown) that may be utilized to pull, rather than push, the intramedullary nail (100) out of the bone, once inserted, if needed. Locking screw (300) (See FIG. 4) may optionally serve as a removal tool. The leading end (103) may also optionally include a tapered tip (108) to ease insertion of the nail into the bone (See FIGS. 1A,1B).

The elongated shaft (101) may also include threaded or unthreaded cross-drilled holes (110,111) for insertion of locking screws (not shown).

Figure 2:
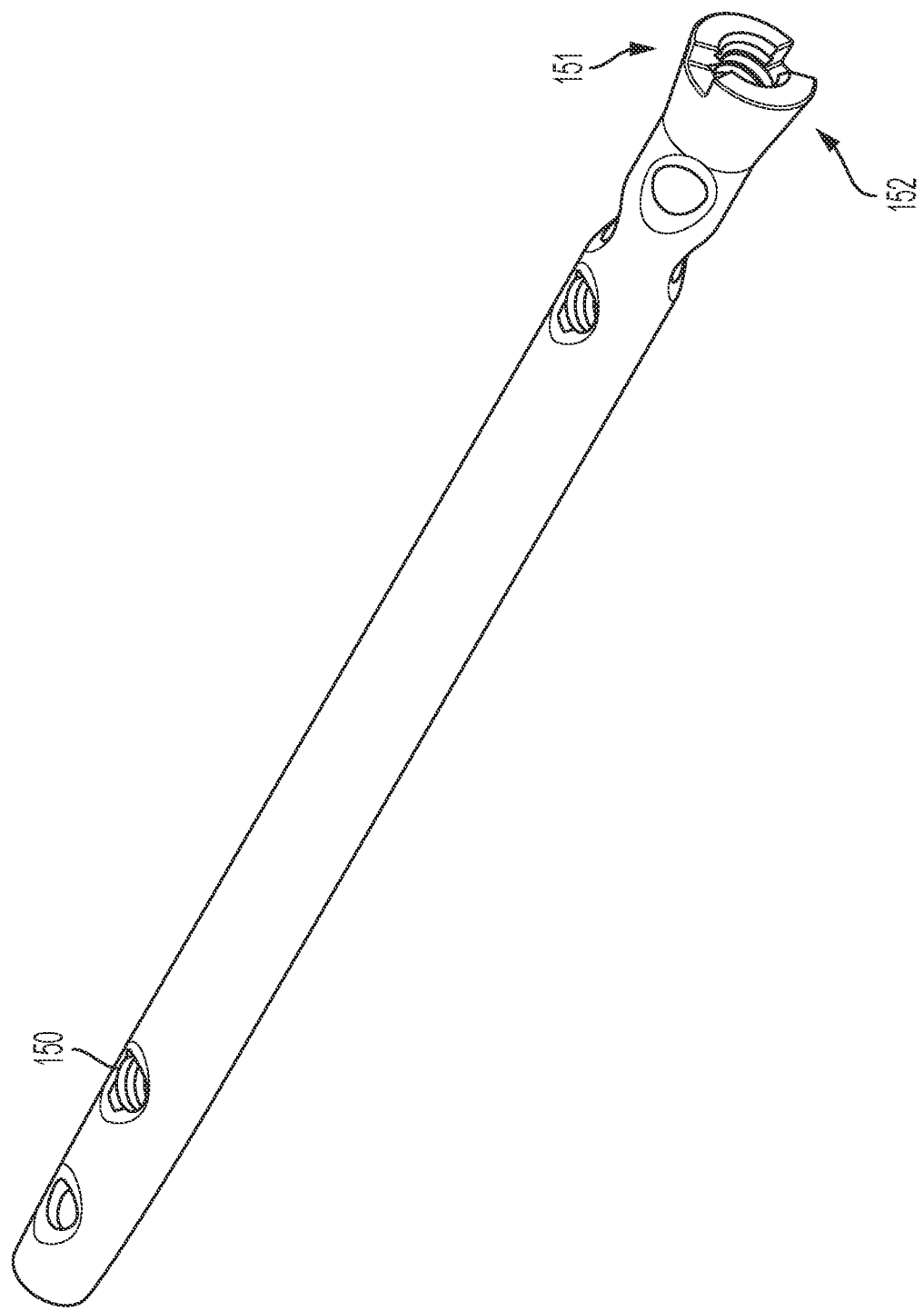
FIG. 2 is an isometric view of an additional embodiment of the intramedullary nail of the present invention having an optional tapered trailing end.

In an alternative embodiment of the intramedullary nail (150), shown in FIG. 2, the trailing end (151) may optionally include a flared section (152) to provide additional strength, and to ensure proper mating with the mating feature (204) of combination drill guide/insertion handle (200) (See FIG. 3B) in the case of intramedullary nails of smaller diameters.

Referring next to FIG. 3A, therein are shown several views of a combination drill guide/insertion handle (200) according to one embodiment of the present invention. The combination drill guide/insertion handle (200) is generally L-shaped comprising a vertical handle portion (201) and a horizontal drill guide portion (202). The vertical handle portion (201) and drill guide portion (202) may be of unitary construction or may comprise two or more components that are assembled together to form the combination drill guide/insertion handle. At the bottom of the vertical handle portion (202) is a horizontal mandrel (203) which can optionally taper partially or completely towards its tip (204). Tip (204) of mandrel (203) is adapted to mate with anti-rotational feature (106) of intramedullary nail (100) (See FIG. 1A).

Combination drill guide/insertion handle (200) additionally comprises an orifice (205) extending from the rear of the vertical handle (201), through the mandrel (203), and through the tip (204) of the mandrel (203). Orifice (205) is adapted to accept locking screw (300) (See FIG. 4) in order to secure the intramedullary nail (100) to the combination drill guide/insertion handle (200).

Figure 7A:
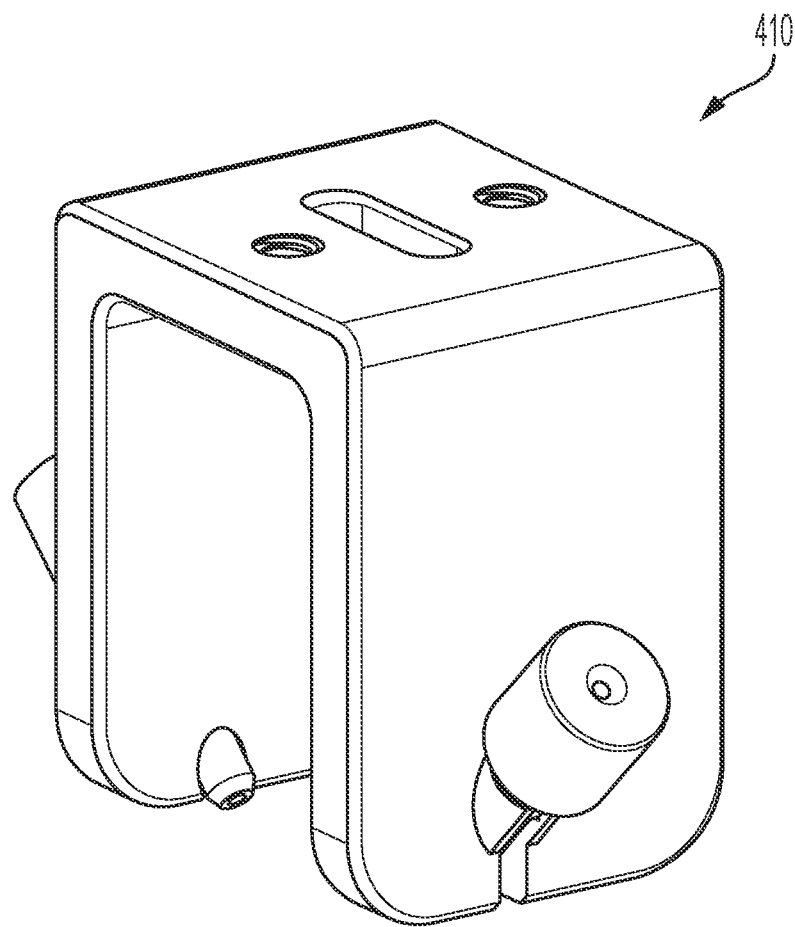
FIGS. 7A and 7B illustrate guides used to assist in drilling bone holes matching oblique or transversal cross-drilled screw holes on the intramedullary nail of the present invention.
Figure 7B:
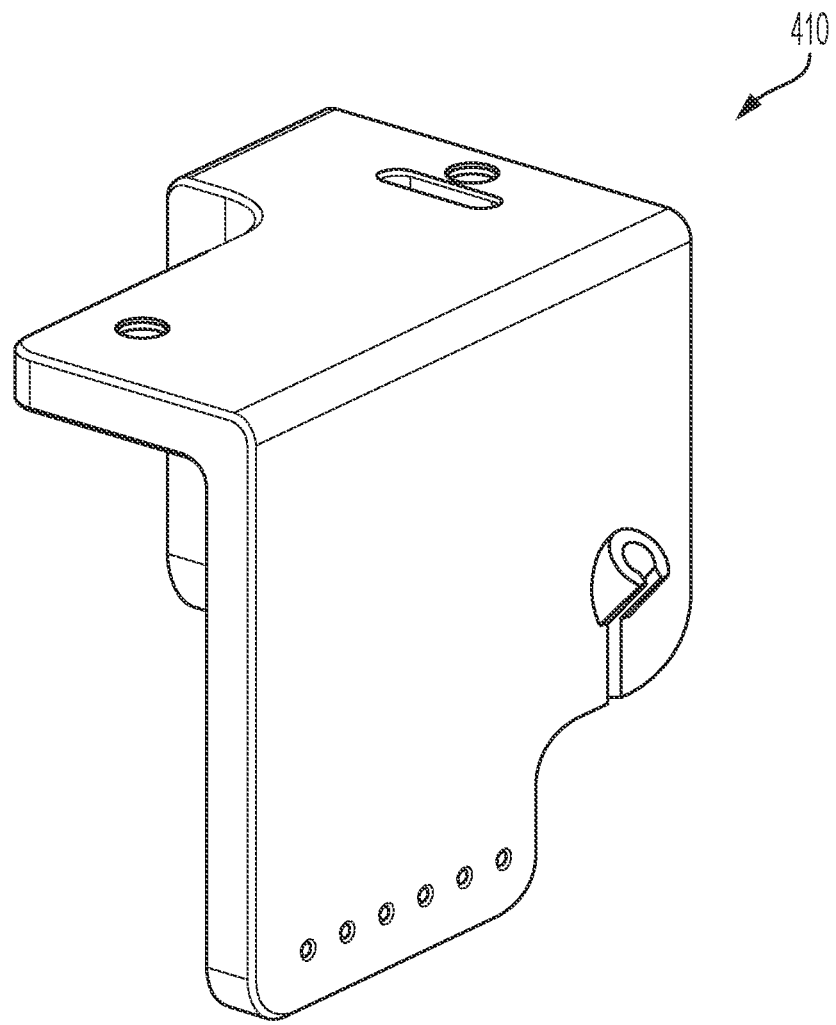
Figure 8A:
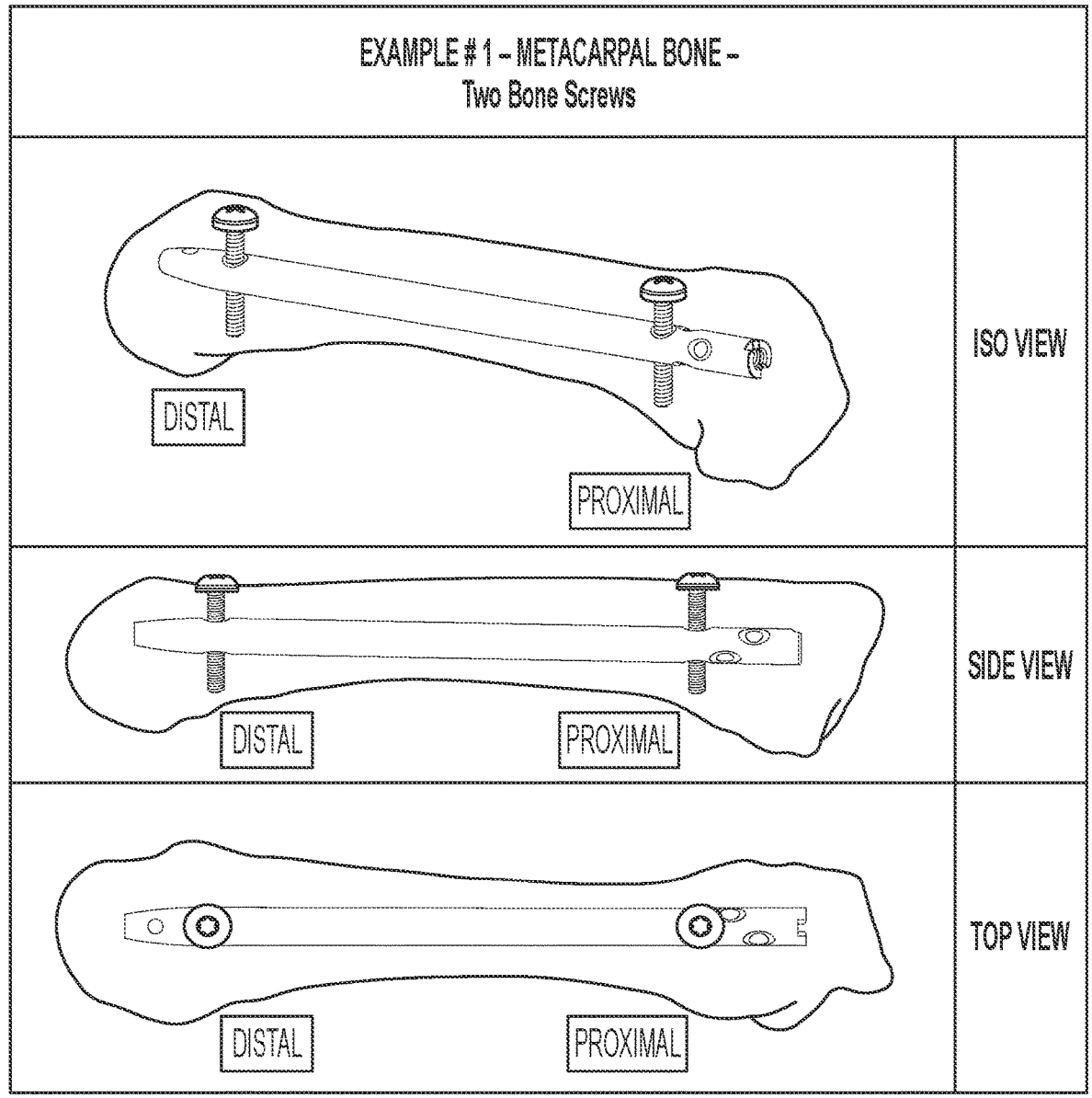
FIGS. 8A, 8B, and 8C are illustrations of embodiments of the intramedullary nail of the present invention implanted on metacarpal and phalanx bones using different types of screws.
Figure 8B:
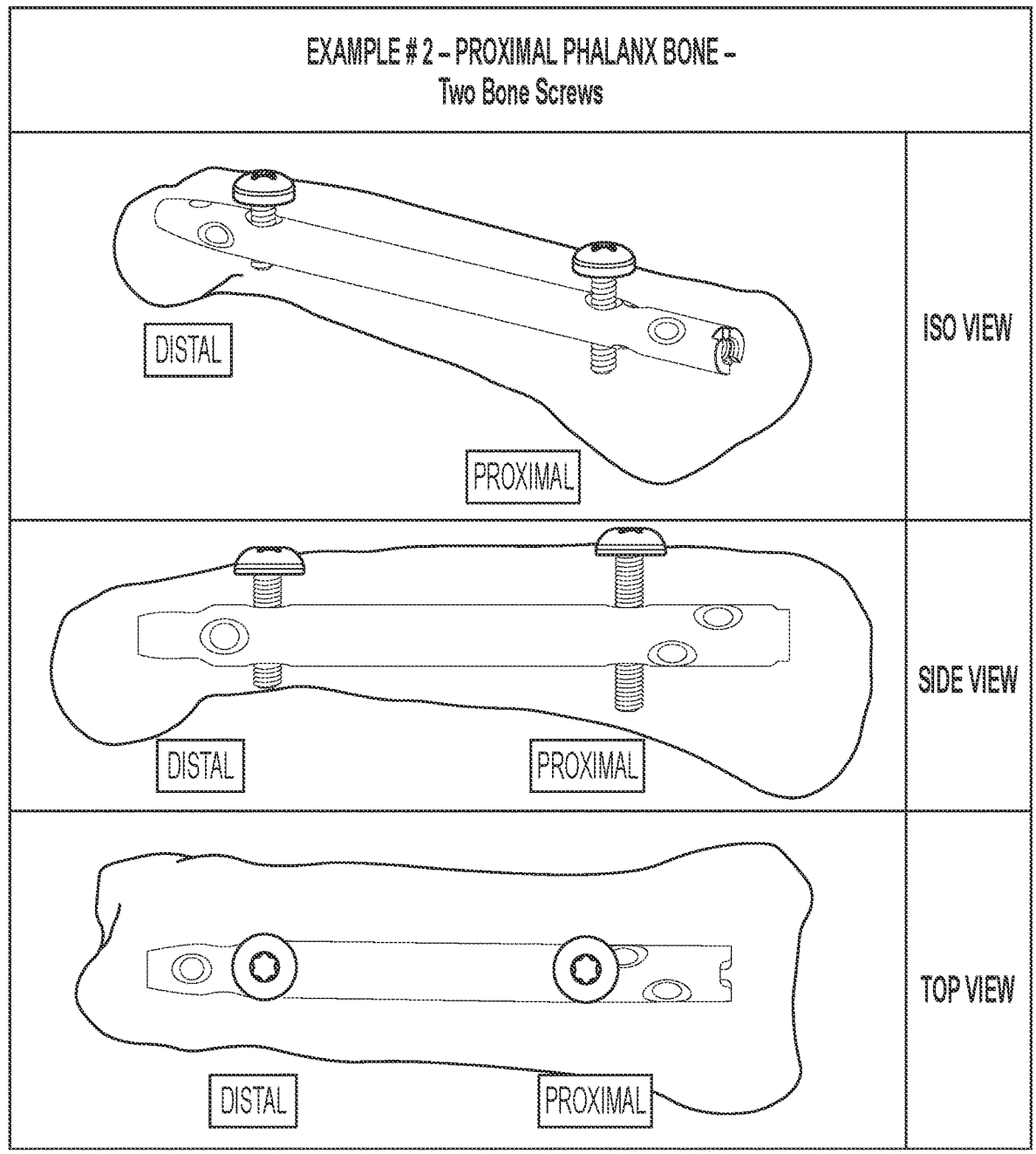
Figure 8C:
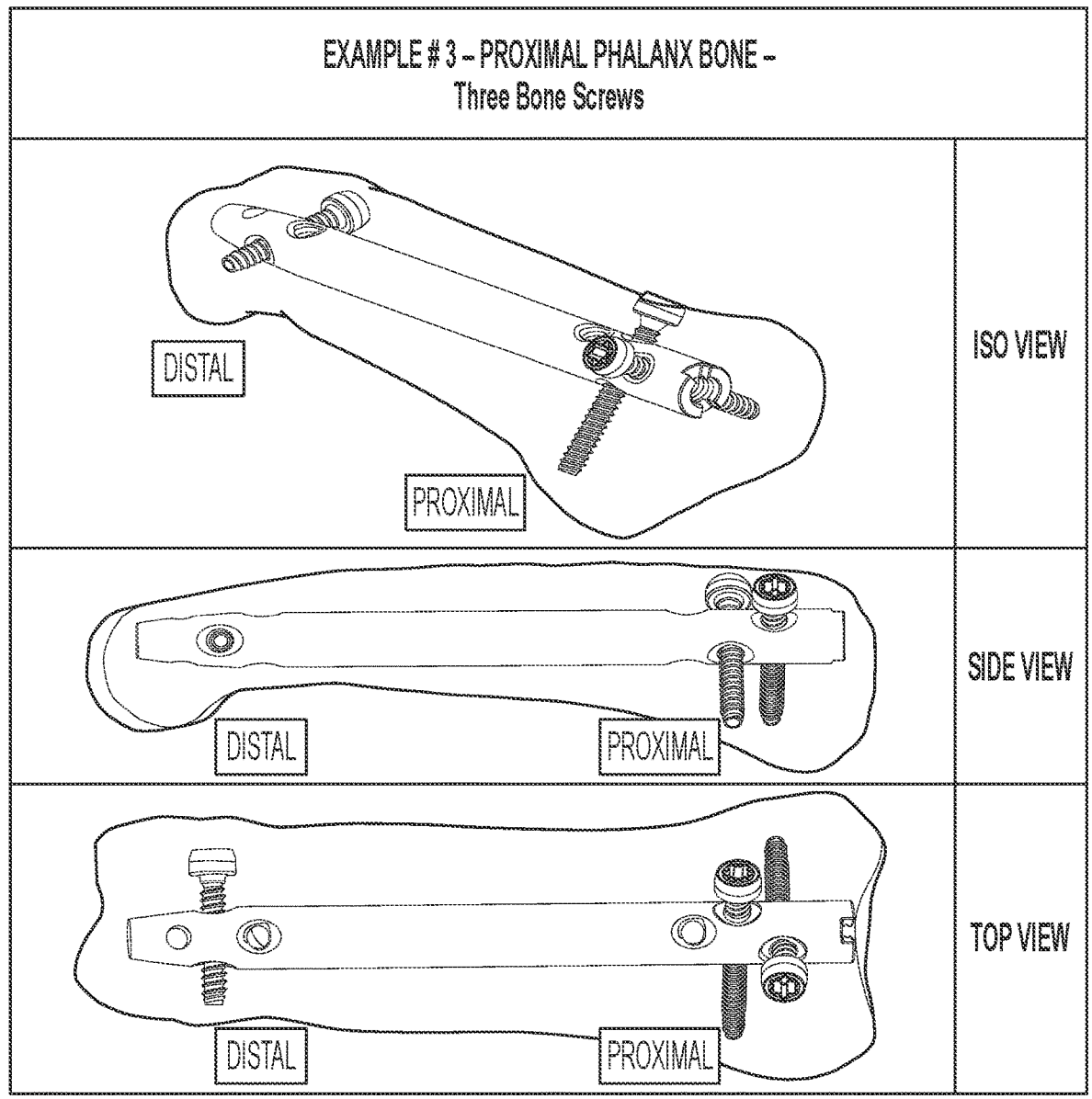

Combination drill guide/insertion handle (200) also comprises one or more drill slots (206). When intramedullary nail (100) is attached to mandrel tip (204), with locking screw (300), one or more of the drill slots on the drill guide/insertion handle are aligned with one or more corresponding locking compression screw holes (110, FIG. 1A) of the intramedullary nail. The drill slots are thus used to precisely drill openings in the bone for locking compression screws which mate with the threaded vertical holes (110) (See FIGS. 1A, 1B, and 8). An additional drilling guide (410) that can be attached to the combination drill guide/insertion handle (200) may be used to similarly, and precisely, drill openings in the bone for transfixion screws that are obliquely or transversally oriented on the intramedullary nail, in alignment with transfixion screw holes (111). Examples of such a guide are shown in FIGS. 7A and 7B, and the final result is shown in FIGS. 8A, 8B, and 8C.

The combination drill guide/insertion handle (200) may be manufactured as a single component or may be modular to separate the drill guide portion from the insertion handle. If the device is manufactured as two separate components, the drill guide and insertion handle can be locked to, and unlocked from, each other through a variety of means, including an optional top connecting screw (207).

Figure 4:
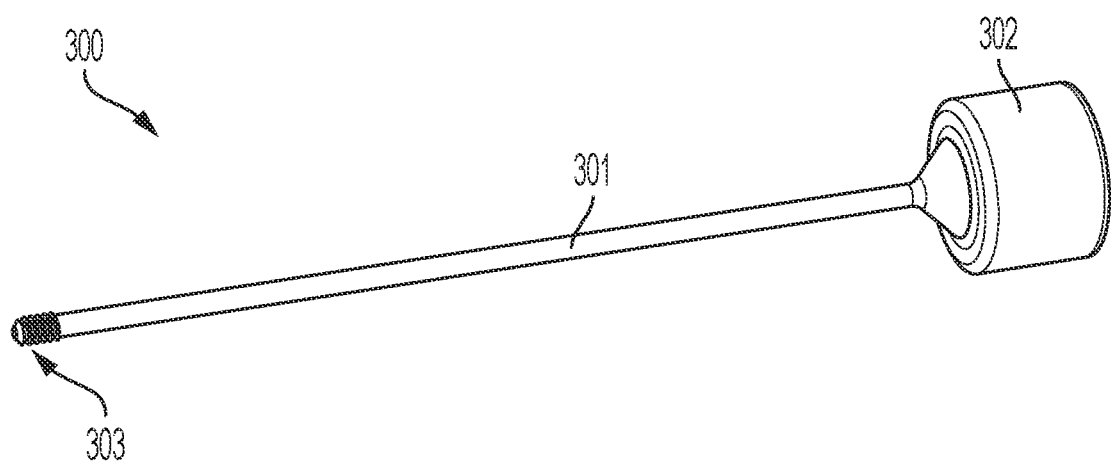
FIG. 4 illustrates the locking screw used to attach the intramedullary nail to the combination drill guide/insertion handle
Figure 5:
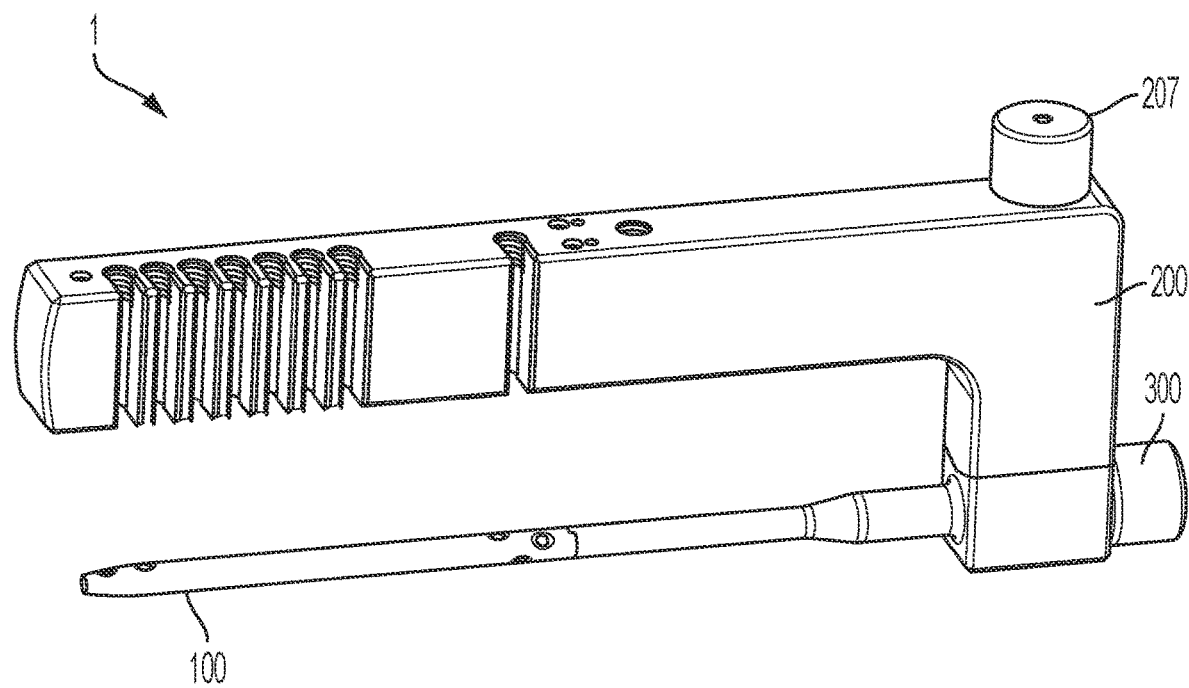
FIG. 5 illustrates an assembled view of an intramedullary nail, combination drill guide/insertion handle, and locking screw according to the present invention.
Figure 6:
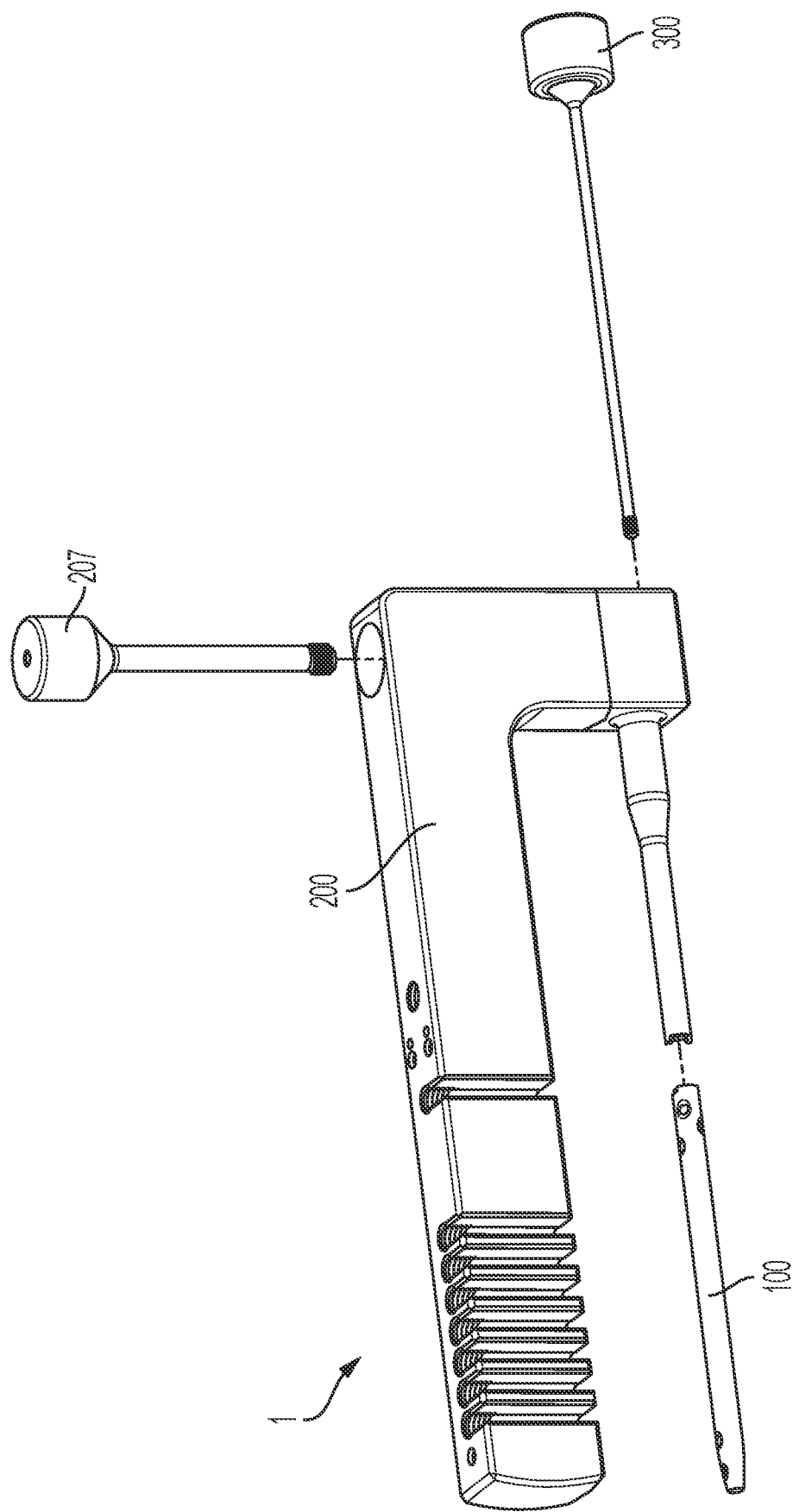
FIG. 6 illustrates an exploded view of an intramedullary nail, combination drill guide/insertion handle, and locking screw according to the present invention.

Referring next to FIG. 4, shown is locking screw (300) which locks intramedullary nail (100) with combination drill guide/insertion handle (200) as shown in FIGS. 5 and 6.

Connecting screw (300) comprises an elongated shaft (301) extending from a knob (302) to connecting screw tip (303). Knob (302) may optionally be knurled to ease turning same with fingers. Alternatively, instead of knob (302), connecting screw can be further tightened by a driver instrument (not shown). Locking screw tip (303) comprises an external thread that is adapted to mate with the internal thread internal thread (105) of the trailing end (104) of intramedullary nail (100) and also optionally with the internal thread (109) of the leading end (103) of intramedullary nail (100).

Referring next to FIGS. 5 and 6, shown are assembled and exploded views of the complete intramedullary nail system assembly (1) which further illustrate how the intramedullary nail (100), combination drill guide/insertion handle (200) and connecting screw (300) are designed to mate. As previously noted, top connecting screw (207) is optional and not needed in embodiments where the combination drill guide/insertion handle (200) where the same is of unitary construction.

FIGS. 8A, 8B, and 8C illustrate examples of embodiments of the intramedullary nail of the present invention implanted on metacarpal and phalanx bones using different types of screws.

Method of Use

An exemplary procedure for insertion of the disclosed intramedullary nail generally consists of the following steps (the dimensions referenced here are for a 4.0 mm diameter nail and should not be considered limiting for differently sized nails):

(1) An 8-inch long, 1.6 mm K-Wire is inserted through the intramedullary canal of the bone to be treated while aligning distal and proximal fragments of the fracture. This centralizes the location of the nail within the canal of the bone. Both ends of the K-Wire should extend past the length of the bone and soft tissue.

(2) With the K-Wire remaining in place, begin reaming over the 1.6 mm K-Wire with a cannulated awl first to just past the cortical bone of the base of the bone. Then ream with a 2.7 mm cannulated reamer from proximal to distal up to the intended location of the distal end of the nail implant.

(3) After reaming with the 2.7 mm cannulated reamer, continue reaming with the next sequential reamer, 3.3 mm up to the same location as reamed by the 2.7 mm reamer. If 3.3 mm reamer size is felt sufficient, then a 3.0 mm Nail is chosen. However, if a 3.3 mm reamer is not felt as sufficient for the medullary canal of the bone, then subsequently ream with a 3.8 mm and a 4.3 mm cannulated reamer for either a 3.5 mm Nail or a 4.0 mm Nail, respectively.

(4) Attach the nail to the combination drill guide/insertion handle by using a locking screw that mates with a thread at the proximal end of the nail.

(5) Mate the well or cup in the distal end of the nail with the tip of the K-Wire which remains inserted within the medullary canal of the bone. As the nail is inserted, it will push the 1.6 mm K-Wire out while simultaneously taking its place within the bone.

(6) Once nail is inserted to its final place within the bone, drill a vertical hole into the bone through the nail's locking compression screw hole using a 1.4 mm K-Wire by using the marked drilling guide locations (not shown) (distal-based on nail length and proximal) engraved on the combination drilling guide/insertion handle. The 1.4 mm K-Wire should penetrate the bone from the near cortex and extend through one of the vertical holes on the nail's shaft up to the far cortex of the bone.

(7) Insert an appropriately sized locking compression screw into the drilled cross-hole and tighten to lock the nail into position.

(8) Optionally, cross-holes, oriented at 45° and 90° can be drilled and, additional screws can be inserted, using other marked drilling guide adapter locations (not shown).

Although described above in connection with certain bone shapes, nail diameters, and screw types these descriptions are not intended to be limiting as various modifications may be made therein without departing from the spirit of the invention and within the scope and range of equivalent of the described embodiments.

We claim:

1. An intramedullary nail comprising:
    a solid shaft having first and second opposing ends, a length, a diameter, and an exterior bone contacting surface;
    a leading end adjacent to the first opposing end, the leading end progressively tapering from the first opposing end and terminating in a cup, the cup adapted to receive a tip of a k-wire inserted in a bone, and push out the k-wire upon insertion of the intramedullary nail into the bone;
    a trailing end adjacent to the second opposing end, the trailing end terminating in a fitting adapted for attachment to a driving tool;
    wherein the shaft, the leading end, and the trailing end are adapted for insertion into the medulla of the bone and form a single, unitary component.

2. The intramedullary nail of claim 1 wherein the cup of the leading end further comprises internal threads.

3. The intramedullary nail of claim 2 wherein the internal threads of the cup of the leading end are adapted to mate with an externally threaded removal tool.

4. The intramedullary nail of claim 1 wherein the trailing end further comprises internal threads.

5. The intramedullary nail of claim 4 wherein the internal threads of the trailing end are adapted to mate with an externally threaded insertion handle.

6. The intramedullary nail of claim 1 wherein the shaft further comprises one or more cross drilled holes.

7. The intramedullary nail of claim 6 wherein at least one of the one or more cross drilled holes is at least partially threaded.

8. The intramedullary nail of claim 6 wherein at least one of the one or more cross drilled holes is unthreaded.

* * * * *